(12) United States Patent
Breindel et al.

(10) Patent No.: US 11,219,747 B2
(45) Date of Patent: Jan. 11, 2022

(54) IV CATHETER WITH VEIN ENTRY INDICATION

(71) Applicant: SMITHS MEDICAL ASD, INC., Plymouth, MN (US)

(72) Inventors: Jay T Breindel, Plymouth, MN (US); Harsh D Chheda, Plymouth, MN (US); David J Goral, Plymouth, MN (US); Thomas T Koehler, Plymouth, MN (US); James Muskatello, Plymouth, MN (US)

(73) Assignee: SMITHS MEDICAL ASD, INC., Plymouth, MN (US)

( * ) Notice: Subject to any disclaimer, the term of this patent is extended or adjusted under 35 U.S.C. 154(b) by 138 days.

(21) Appl. No.: 16/486,126

(22) PCT Filed: Mar. 6, 2018

(86) PCT No.: PCT/US2018/021143
§ 371 (c)(1),
(2) Date: Aug. 14, 2019

(87) PCT Pub. No.: WO2018/165157
PCT Pub. Date: Sep. 13, 2018

(65) Prior Publication Data
US 2020/0230368 A1 Jul. 23, 2020

Related U.S. Application Data

(60) Provisional application No. 62/518,702, filed on Jun. 13, 2017, provisional application No. 62/492,348, (Continued)

(51) Int. Cl.
*A61M 25/06* (2006.01)

(52) U.S. Cl.
CPC .... *A61M 25/0631* (2013.01); *A61M 25/0606* (2013.01); *A61M 25/0693* (2013.01)

(58) Field of Classification Search
CPC .......... A61M 25/0631; A61M 25/0606; A61M 25/0693; A61M 25/06
See application file for complete search history.

(56) References Cited

U.S. PATENT DOCUMENTS 3,335,723 A * 8/1967 Waldman, Jr. ..... A61M 25/0111
604/163
3,352,306 A 11/1967 Hirsch
(Continued)

FOREIGN PATENT DOCUMENTS

EP 0993839 4/2000
EP 0993839 A1 * 4/2000 ........ A61M 25/0097
(Continued)

OTHER PUBLICATIONS

EUIPO; Search Report dated Sep. 24, 2020 in EP Application No. 18763871.3.
(Continued)

*Primary Examiner* — Laura A Bouchelle
(74) *Attorney, Agent, or Firm* — Snell & Wilmer L.L.P.

(57) ABSTRACT

An intravenous catheter assembly that includes a catheter tube and an introducer needle that is disposed, at least in part, within the catheter tube when the introducer needle is in a ready for use position. The introducer needle includes a lateral surface that defines a relief that is positioned under the distal end of the catheter tube when the introducer is in the ready for use position to provide a flow path into a flash indication space.

8 Claims, 6 Drawing Sheets

Related U.S. Application Data filed on May 1, 2017, provisional application No. 62/467,397, filed on Mar. 6, 2017.

(56) References Cited

U.S. PATENT DOCUMENTS

| | | | |
|---|---|---|---|
| 4,755,356 A | | 7/1988 | Robbins et al. |
| 5,558,651 A | * | 9/1996 | Crawford .......... A61M 25/0618 604/110 |
| 5,697,014 A | | 12/1997 | Brimhall |
| 5,810,780 A | * | 9/1998 | Brimhall .......... A61M 25/0693 604/167.02 |
| 6,497,994 B1 | | 12/2002 | Kafrawy |
| 6,527,747 B2 | | 3/2003 | Adams et al. |
| 7,597,681 B2 | | 10/2009 | Sutton et al. |
| 7,736,337 B2 | | 6/2010 | Diep et al. |
| 8,979,803 B2 | | 3/2015 | Darr |
| 2002/0107483 A1 | | 8/2002 | Cook |
| 2003/0105431 A1 | | 6/2003 | Howell |
| 2004/0215146 A1 | | 10/2004 | Lampropoulos et al. |
| 2004/0267200 A1 | | 12/2004 | Carlyon et al. |
| 2005/0015071 A1 | | 1/2005 | Brimhall |
| 2005/0075606 A1 | | 4/2005 | Botich et al. |
| 2008/0300543 A1 | | 12/2008 | Abriles et al. |
| 2010/0305519 A1 | * | 12/2010 | McKinnon .......... A61M 25/0612 604/272 |
| 2011/0054402 A1 | | 3/2011 | Tanabe et al. |
| 2011/0054403 A1 | * | 3/2011 | Tanabe .......... A61M 5/158 604/164.01 |
| 2012/0136311 A1 | | 5/2012 | Knutsson |
| 2012/0323181 A1 | | 12/2012 | Shaw et al. |
| 2015/0151084 A1 | | 6/2015 | Teoh |
| 2016/0106959 A1 | | 4/2016 | Woehr |
| 2016/0220161 A1 | | 8/2016 | Goral et al. |
| 2016/0220791 A1 | | 8/2016 | Akcay et al. |
| 2016/0228683 A1 | | 8/2016 | Tietze |
| 2016/0310704 A1 | | 10/2016 | Ng et al. |
| 2016/0354539 A1 | | 12/2016 | Tan et al. |
| 2017/0120010 A1 | * | 5/2017 | Burkholz .......... A61M 39/0606 |
| 2017/0354799 A1 | * | 12/2017 | Gupta .............. A61M 25/0606 |
| 2018/0028788 A1 | | 2/2018 | Belson |
| 2018/0339131 A1 | | 11/2018 | Muse et al. |

FOREIGN PATENT DOCUMENTS

| | | |
|---|---|---|
| JP | 2006055674 | 3/2006 |
| WO | 9614894 | 5/1996 |
| WO | 1999052584 | 10/1999 |
| WO | 2001056642 | 8/2001 |
| WO | 2002096494 | 12/2002 |
| WO | 2017074684 | 5/2017 |

OTHER PUBLICATIONS

EUIPO; Search Report dated Sep. 27, 2020 in EP Application No. 18764834.0.
ISA; International Search Report and Written Opinion PCT Application No. PCT/US2020/021485 dated May 5, 2020.
International Search Report and Written Opinion PCT Application No. PCT/US18/021135 dated May 16, 2018.
International Search Report and Written Opinion PCT Application No. PCT/US18/021143 dated May 11, 2018.
International Search Report and Written Opinion PCT Application No. PCT/US18/021155 dated Apr. 27, 2018.
USPTO; Non-Final Office Action dated Apr. 13, 2021 in U.S. Appl. No. 16/486,108.

* cited by examiner

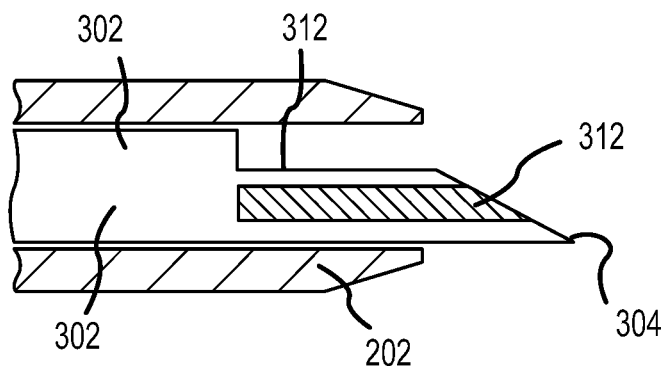
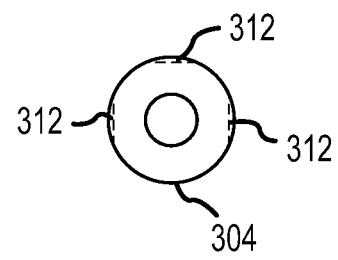
FIG.4a     FIG.4b
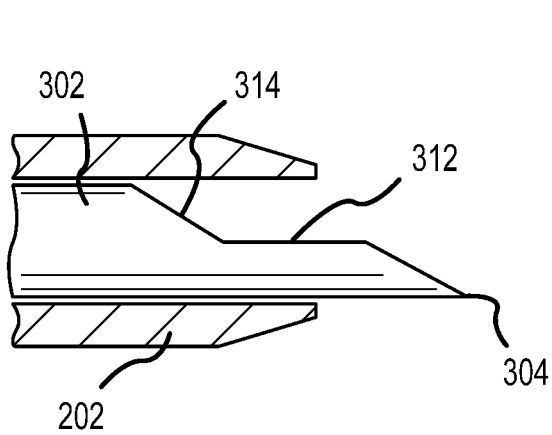
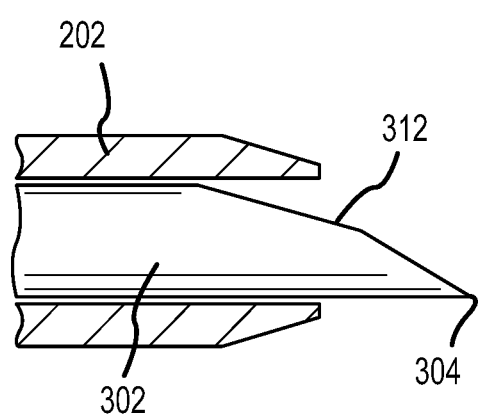
FIG.5     FIG.6

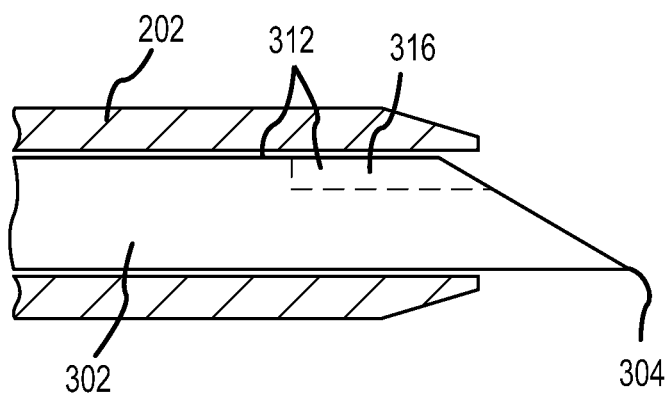 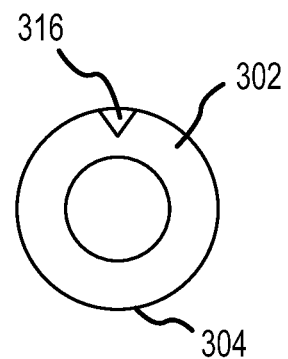
FIG.7a  FIG.7b
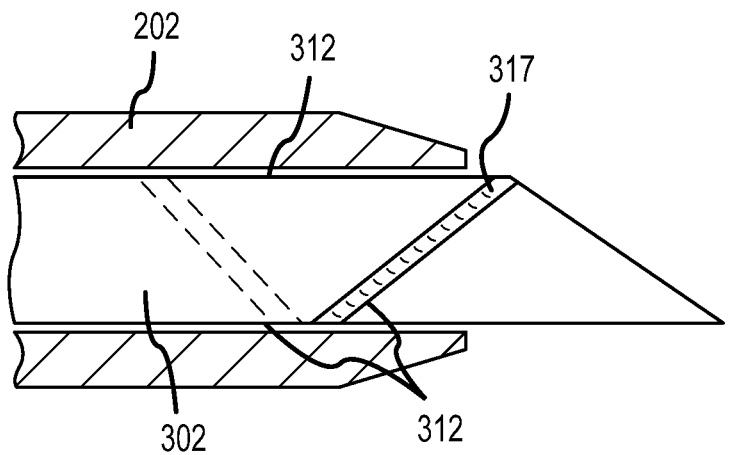
FIG.8

US 11,219,747 B2

IV CATHETER WITH VEIN ENTRY INDICATION

CROSS-REFERENCE TO RELATED APPLICATIONS

This application is U.S. national phase filing under 35 U.S.C. § 371 of PCT/US2018/21143 (the "143 application") filed on Mar. 6, 2018 and titled "IV CATHETER WITH VEIN ENTRY INDICATION." The '143 application claims priority from U.S. Ser. No. 62/467,397 filed on Mar. 6, 2017 and titled "PERIPHERAL IV CATHETER," U.S. Ser. No. 62/492,348 filed on May 1, 2017 and titled "IV CATHETER WITH VEIN ENTRY INDICATION," and U.S. Ser. No. 62/518,702, filed on Jun. 13, 2017 and titled "IV CATHETER WITH VEIN ENTRY INDICATION." All of the aforementioned applications are incorporated herein by reference in their entirety for all purposes.

FIELD

The present disclosure relates to intravenous (IV) catheters and more particularly to IV catheters that include features to provide an early indication of needle or catheter entry into a vein.

RELATED ART

Safety catheter assemblies typically include a catheter and a catheter introducer having an introducer needle. The catheter is provided assembled to the introducer in a ready for use configuration with a tube of the catheter positioned over the introducer needle and a sharp tip of the introducer needle protruding from a distal end of the catheter. A needle sheath may be positioned over the sharp tip of the insertion needed to prevent unwanted needle sticks prior to the catheter assembly being used. The overall safety catheter assembly, including the catheter, catheter introducer, and needle sheath, may be provided for use in a sterilized and assembled state, contained within a sealed package. One example of such a safety catheter includes the JELCO INTUITIV (Trademark) safety catheter marketed by Smiths Medical ASD, Inc. of Plymouth, Minn., as described in U.S. Pat. No. 8,257,322.

To insert the catheter into the vein of a subject, a clinician first removes the safety catheter assembly from the packaging. The needle sheath is removed to expose the sharp tip of the introducer needle that is protruding from the distal end of the catheter. The clinician punctures an identified site of a subject with the sharp needle tip and urges the introducer needle forward until the needle tip enters the vein of the subject. An initial amount of blood may pass through a lumen of the needle, entering the catheter and/or catheter introducer where the clinician may view the "flashback" of the blood to confirm entry into the vein. The catheter may then be moved distally over the needle to thread the tube of the catheter into position in the vein of the subject. With the catheter positioned as desired, the clinician withdraws the needle by pulling the catheter introducer proximally away from the subject while holding the catheter generally stationary with respect to the subject until the needle and introducer are separated from the catheter. Safety features may be actuated, passively or actively, during needle withdrawal to prevent access to the sharp needle tip once withdrawn from the catheter. The clinician may dispose of the catheter insertion device in a sharps container, after the insertion device is separated from the catheter.

Some catheter assembly include a needle having a notch or window on a lateral side of needle, proximal to the distal end of the needle. The notch is positioned in the catheter tube when the catheter assembly is in the ready for use position. When a clinician introduces the needle tip into the vein of a subject, flashback blood passes up the needle lumen, out of the notch and into the annular space between the catheter and needle. The presence of flashback blood in this space can provide the clinician with a desirable, early, visible indication of entry into the vein of a subject.

BRIEF DESCRIPTION OF THE FIGURES

In the drawings, different embodiments of the invention are illustrated in which:

FIGS. 4a and 4b are a partial, cross sectional side view and a distal view, respectively, of a catheter tube and an introducer needle that includes a plurality of reliefs positioned on different lateral sides of the needle (catheter tube omitted from FIG. 4b), according to one example embodiment.

FIG. 5 is a partial, cross sectional side view of a catheter tube and an introducer needle that includes a sloped transition in relation to a longitudinal axis of the introducer needle.

FIG. 6 is a partial, cross sectional side view of a catheter tube and an introducer needle that includes a sloped relief in relation to a longitudinal axis of the introducer needle.

FIGS. 7a and 7b are a partial, cross sectional side view and a distal view, respectively, of a catheter tube and an introducer needle that includes a plurality of relief having a groove, according to one example embodiment.

FIG. 8 is a partial, cross sectional side view of a catheter tube and an introducer needle that includes a spiral groove, according to one example embodiment.

DETAILED DESCRIPTION

Some IV catheter assemblies include introducer needles having a notch or window structure that allows flashback blood to enter the annular flash space between a catheter tube and the introducer needle. The presence of flashback blood in this annular space can provide a clinician with an early, visible indication that a needle has entered a vein. The notch, however, may create a leak path for blood to escape outside of catheter assemblies, particularly for catheter assemblies that include a septum that is intended to seal the path that provides entry into the introducer needle. Some approaches to sealing this leak path have included lengthening the septum. Disclosed herein is an introducer needle having a relief that allows flashback blood to flow directly into the flash space by passing from the vein of the subject and directly into the flashback space that lies between the introducer needle and the catheter without having to enter the lumen of the introducer needle. Such a configuration can allow catheter design optimization without a lengthened septum.

Figure 1A:
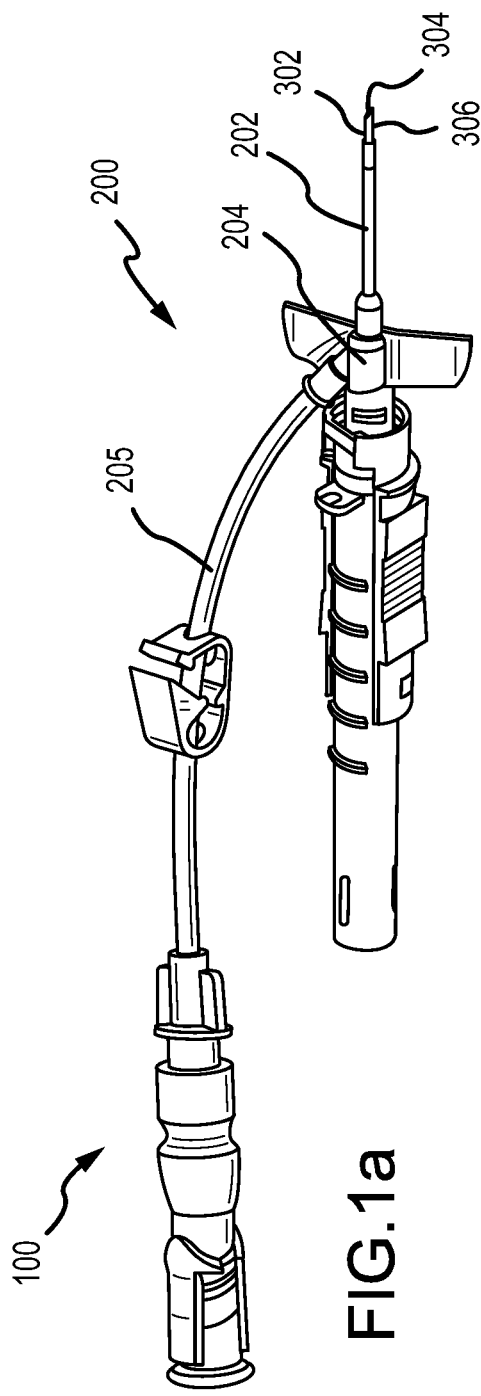
FIGS. 1a and 1b are perspective views of a catheter assembly in each of a ready for use position and a safe position, respectively, according to one example embodiment.
Figure 1B:
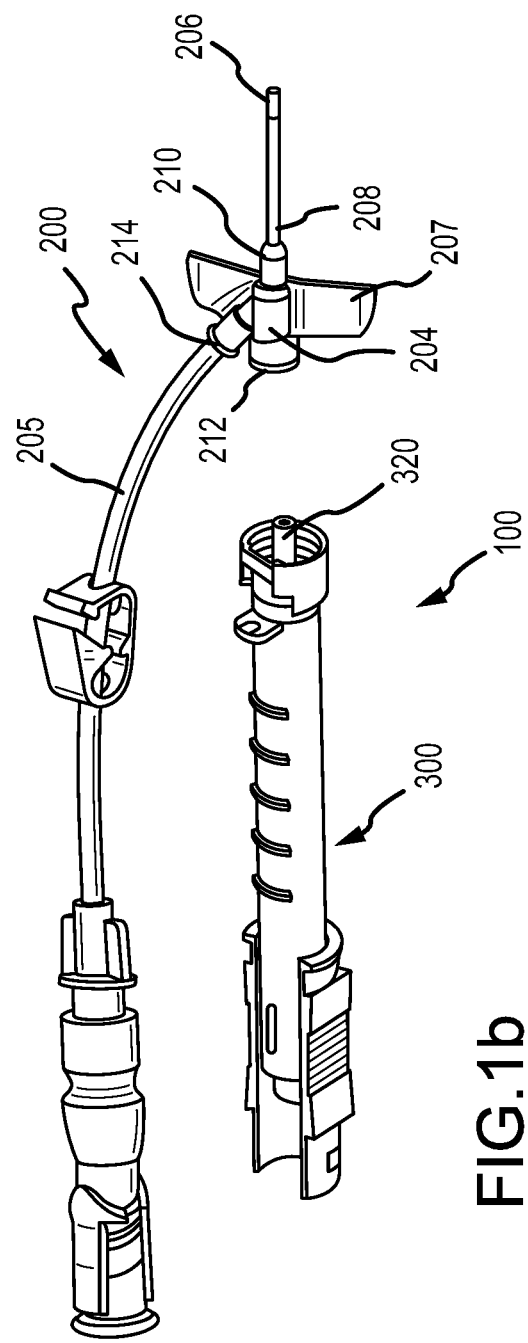

Turn now to the figures, and initially FIGS. 1a and 1b that show an example embodiment of a catheter assembly 100 that includes a catheter 200 and a catheter introducer 300. FIG. 1a shows the catheter assembly 100 in a ready position, as configured ahead of a clinician initiating a catheter insertion procedure. FIG. 1b shows the catheter assembly 100 in a safe position with the catheter 200 separated from the catheter introducer 300 and access to the sharp tip of the introducer needle prevented by a safety device 320.

The catheter 200 includes a catheter tube 202, a catheter hub 204, and an extension tube 205 that cooperate to provide a fluid pathway between the vein of a subject and other IV fluid components, such as an IV fluid supply. The catheter tube 202 includes a distal end 206, a proximal end 208, and a lumen extending there between. The catheter hub 204 includes a distal end 210, a proximal end 212 and a side port 214, in the illustrated example embodiment. The illustrated example embodiment also includes over molded wings 207 that may help stabilize the catheter hub against a subject's skin. The proximal end 212 of the catheter tube 202 is connected to the distal portion 210 of the catheter hub. The side port 214 is connected to the extension tube, thereby providing fluid communication from the extension tube, through the catheter hub and into the catheter tube.

Figure 2:
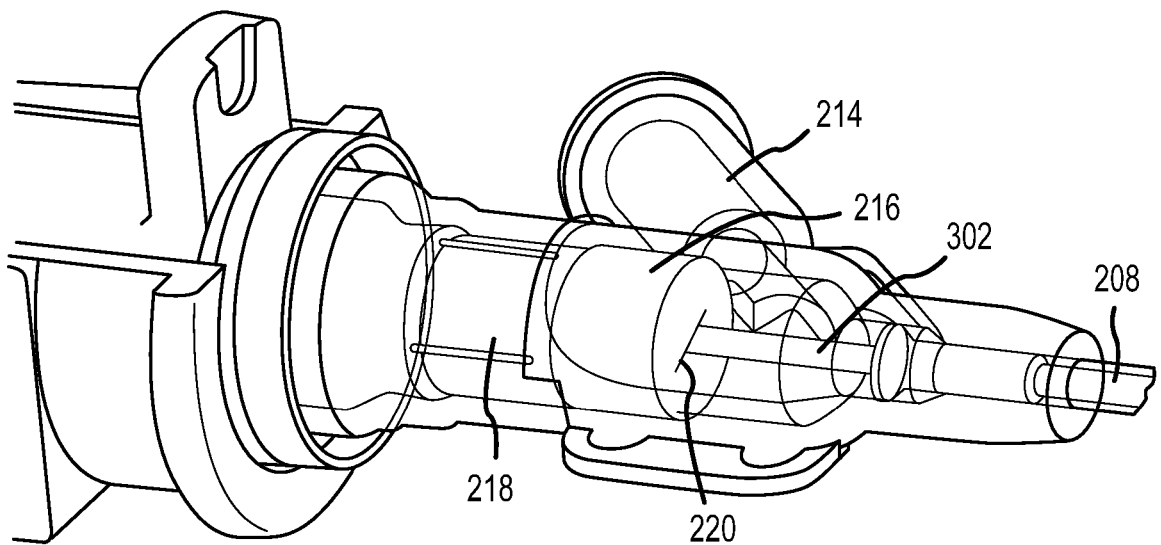
FIG. 2 is a partial view of the example embodiment shown in FIGS. 1a and 1b, showing the catheter hub in a transparent view with over molded wings removed from the view.

FIG. 2 shows a view of the catheter hub of FIGS. 1a and 1b, with the over molded wings 207 removed and the catheter hub drawn in a transparent manner. The proximal end of the catheter hub 212 houses an elastomeric septum 216 that is secured to the catheter hub by a septum retainer 218. The septum 216 provides an access pathway for the introducer needle into the catheter tube and seals the interior of the catheter hub to prevent fluid escape from the catheter hub, both while the introducer needle is present and after the introducer needle is removed. The septum includes a single slit 220 that accommodates the introducer needle in the illustrated example embodiment. It is to be appreciated, however, that alternate embodiments may include multiple slits or no slit at all. The septum may be constructed of silicone, isoprene, or other suitable elastomeric materials.

The septum is secured to the catheter hub by the septum retainer 218. As may be seen in FIG. 2, the septum retainer is received within the catheter hub 204 to position the septum 216 in a manner that prevents proximal movement. One or more shoulders on the interior of the catheter hub may prevent distal movement of the septum within the catheter hub. The septum retainer is secured to the catheter hub by a snap fit connection, although other types of connections are also contemplated.

The catheter introducer 300, in the illustrated example embodiment of FIGS. 1a and 1b, includes an introducer needle 302 having a sharp distal tip 304 that is used to create an entry passageway into the vein of a subject. The introducer needle 302 extends from a sharp distal tip at a distal end 306 to a proximal portion that is connected to a needle hub and defines an internal lumen that extends therebetween. A flash plug (not shown) may be connected to the needle hub 310 and may include a microporous barrier that permits the escape of air but prevents the escape of fluid. In this respect, flashback blood may flow through the needle into the flashplug, providing an additional indication of vein entry.

The catheter introducer 300 includes a needle safety feature 320 that prevents access to the sharp needle tip 304 after the catheter introducer 300 is separated from the catheter 200. The safety feature shown in FIGS. 1a and 1b includes the nose of a needle guard housing that prevents access to the needle tip. It is to be appreciated that the safety device shown in FIGS. 1a and 1b is but one type of safety device that may be utilized. According to alternate embodiments, a tip protector type safety device is utilized that prevents access to the sharp needle tip without preventing access to the needle body, such as the tip protector type safety device shown in either of European Patent No. EP 2 204 204 or U.S. Pat. No. 8,257,322, each of which is incorporated by reference herein in its entirety.

Figure 3A:
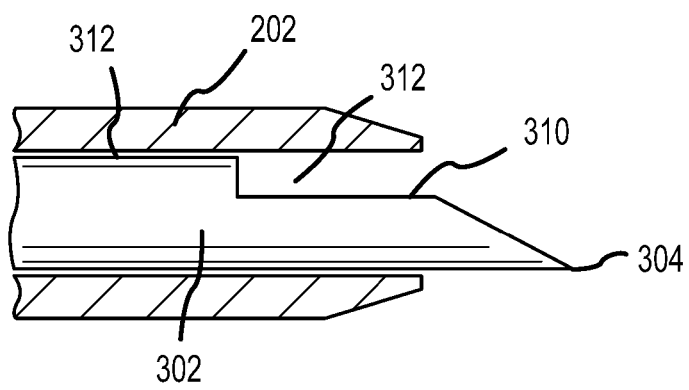
FIGS. 3a and 3b are a partial, cross sectional side view and a distal view, respectively, of a catheter tube and an introducer needle that includes a relief, according to one example embodiment.
Figure 3B:
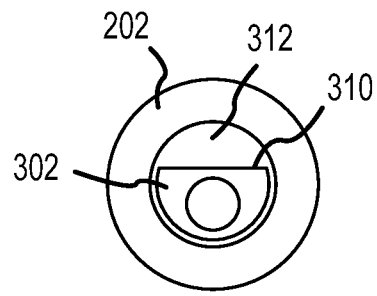

FIGS. 3a and 3b show side and distal views of a catheter tube 202 and an introducer needle 302 having a relief 310 machined into a lateral surface. The relief extends from the distal end of the needle and to a proximal position that lies within the flash space 312 between the introducer needle 302 and catheter tube 202. The relief creates a gap between the distal end of the before and the needle that allows flashback blood entry into the flash space 312. That is, when the as the distal end of the catheter tube enters the vein of a subject, flashback blood may enter the flash indication space through the gap between the introducer needle and the catheter tube at the relief. The distal end of the catheter tube is generally in contact with or close proximity to the introducer needle at other positions, so as to prevent the entry of flashback blood.

The relief shown in FIGS. 3a and 3b is substantially flat, lying across a chord of a cross section of the introducer needle (alternately referred to herein as a cannula) and parallel to the longitudinal axis of the introducer needle. The flat shape of the relief may prove conducive to being formed by a machining process or even a grinding process. It is to be appreciated, however, that other machining or forming processes may alternately be used to create a relief, such as a stamping process, according to some embodiments.

The relief, as shown, lies a consistent depth into the needle at all positions. That is, the relief lies a consistent depth from a tangent to the outer surface of the needle, according to some example embodiments. In such configurations, the radial wall thickness of the needle may vary at different points of the relief, with a central portion of the relief typically having the smallest wall thickness. Generally speaking, reliefs may be constructed and arranged to maintain a minimum wall thickness of at least 0.001 inches, although other configurations are possible. According to some example embodiments that include a 22 gauge needle, may be at a depth of 0.002 inches, 0.003 inches, 0.004 inches, or different depths. These gaps reflect nominal dimensions associated with component parts prior to any sterilization processes.

The relief shown in FIGS. 3a and 3b has a length, taken from a proximal end to a distal end in the direction of the introducer needle that may be greater than the septum of the associated catheter assembly. The elastomeric nature of the septum may allow the septum to conform to both the cylindrical surface of the needle at points proximal to the relief as well as to the cross sectional shape of the needle that includes the relief. In this respect, the presence of the relief may not present a leak path through the septum, unlike a notch. This may enable the septum length and positioning of the relief on the needle to be established without concern or with less concern over leakage that might be caused by the presence of the relief.

The relief may be positioned on different lateral sides of a needle. In the example embodiment of FIGS. 3a and 3b, the relief 312 is positioned on a side of the needle 302 opposite to the needle tip 304. Other configurations are also possible, such as the configuration shown in FIGS. 4a and 4b that includes multiple reliefs 312 positioned on different lateral sides of the needle 302. In this example embodiment, three reliefs are present on the outer surface of the needle. Including additional reliefs that may provide greater overall area for flashback blood to enter the flashback space.

The transition 314 between a relief 312 and other portions of a needle 302 may be configured to promote a smooth withdrawal of the needle through the septum. FIG. 5 shows a cross sectional side view of a relief 312 that transitions smoothly, with an angled surface 314, to the outer, circular circumferential surface of the introducer needle 312. The angled transition 314 surface may reduce the forces involved with needle withdrawal. Additionally or alternately, the smooth transition surface may promote sealing between the needle and the septum.

The relief may be formed at an angle with respect to the longitudinal axis of the introducer needle, as shown in FIG. 6, rather than formed as a flat surface that lies parallel to the needle axis. In such embodiments, the angled relief may provide for a smoother needle withdrawal, similar as described herein with respect to the embodiment of FIG. 5. The angled relief may additionally or alternately promote sealing with the septum. The example embodiment of FIG. 6 combines both an angled relief surface and an angled transition surface to accomplish this. Other embodiments may be constructed differently, such as with a relief having multiple surfaces at different lengthwise positions of the needle and that lie at different angles with respect to the longitudinal axis of the needle.

FIGS. 7a and 7b shows different type of relief that includes a groove 316. As illustrated, the groove is formed or cut in the outer surface of the needle 302 to provide a pathway into the flash indication space 312 that lies between the needle 302 and the catheter 202. According to some embodiments, the groove 316 may be cut deeper and have a narrower width than the relief shown in FIGS. 3a and 3b. This profile may provide greater support for the distal end of the catheter tube 202 at positions adjacent to the groove. During sterilization, this greater support may prevent the distal end of the catheter tube from moving into and blocking the flowpath into the flash indication space. It is to be appreciated that FIGS. 7a and 7b show but one construction of a groove and that others are also contemplated, such as the spiral groove 317 shown in FIG. 8.

Figure 9A:
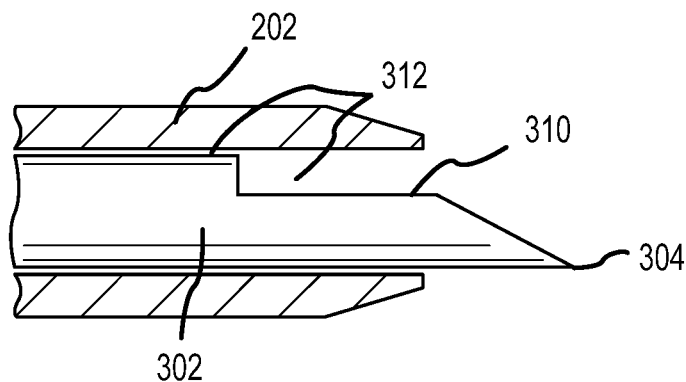
FIGS. 9a and 9b are a partial cross sectional side view and a distal view, respectively, of a catheter tube and an introducer needle that includes a plurality of relief having a flat surface and a slot (catheter tube omitted from FIG. 9b), according to one example embodiment.
Figure 9B:
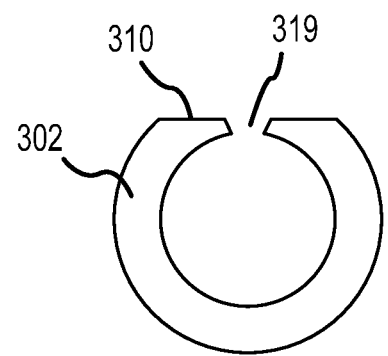

FIGS. 9a and 9b show an example embodiment of a catheter assembly that includes a hollow needle having a relief 310 and a slot 319 that extends through the relief 310, into the lumen of the needle. Both the relief and the slot provide a flowpath to the flash indication space 312 and in this respect, such a configuration may provide a greater area to accommodate flow into the flash indication space. The term "slot", as used herein, refers to a opening in the sidewall of a needle and that extends to a distal end of the needle.

Figure 10A:
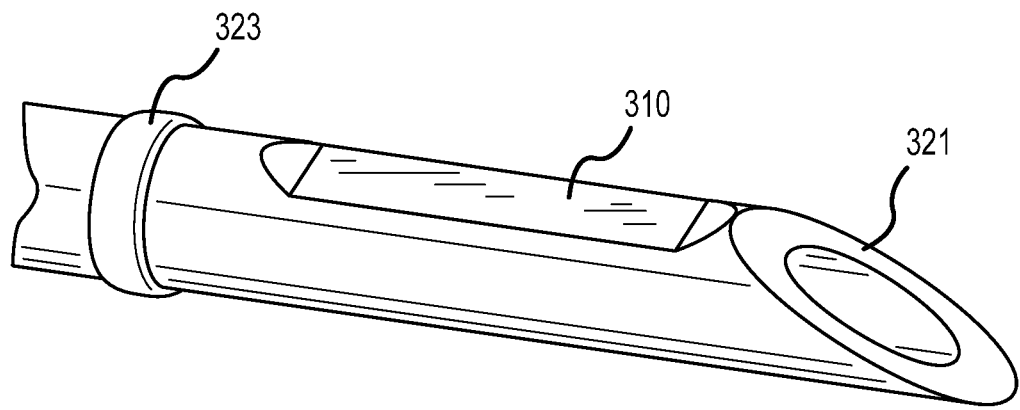
FIGS. 10a and 10b are side and cross sectional views of an introducer needle having a relief positioned proximally to a bevel of an introducer needle, according to one example embodiment.
Figure 10B:
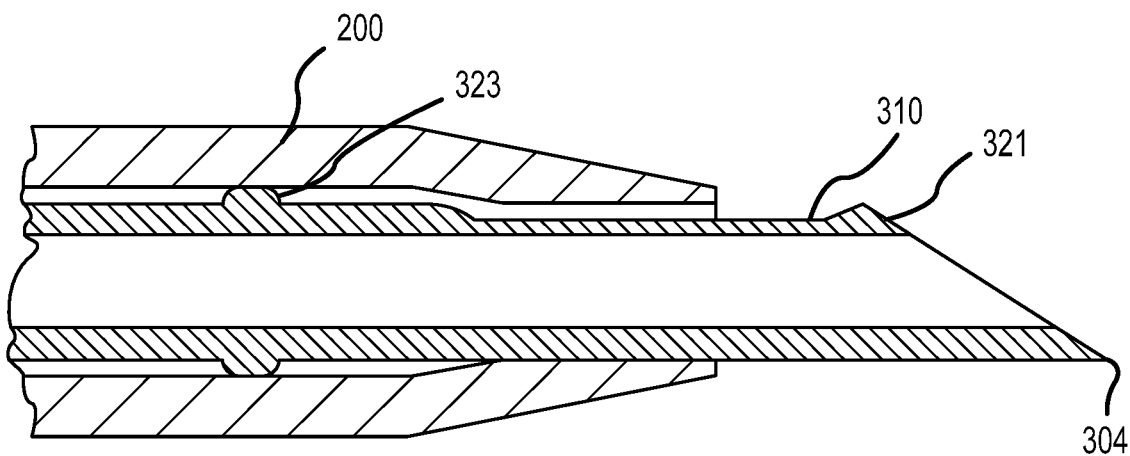

The example embodiments of FIGS. 3a to 9b show reliefs that extend to or through the bevel at the distal tip 304 of the needle 302. In the example embodiment of FIGS. 10a and 10b, the relief is positioned proximally to the bevel 321. Such a configuration may prevent disruption of the distal end of the catheter during the insertion process. The relief is also shown to lie distal to a bump 323 on the needle that is used to actuate a safety mechanism, according to some embodiments.

The needles associated with the example embodiments described herein may have solid or hollow constructions. As may be appreciated, catheter assemblies typically include a hollow introducer needle or cannula having a lumen that provides for the passage of flashback blood. However, the presence of a relief to allow flashback blood to enter the flashback space may facilitate the use of a solid needle that is less complex and/or costly to manufacture.

Various example embodiments of catheters are described herein for use in accessing the vein of a subject. It is to be appreciated, however, that the example embodiments described herein may alternately be used to access the vasculature of a subject at locations other than a vein, including but not limited to the artery of a subject. It is additionally to be appreciated that the term "clinician" refers to any individual that may be performing a catheter insertion procedure with any of the example embodiments described herein or combinations thereof. Similarly, the term "subject", as used herein, is to be understood to refer to an individual or object in which a catheter is to be inserted, whether human, animal, or inanimate. Various descriptions are made herein, for the sake of convenience, with respect to procedures being performed by a clinician to access the vein of a subject, while the disclosure is not limited in this respect.

It is to be appreciated that the term "distal", as used herein, refers to the direction, taking along an axis that lies parallel to the needle of a safety catheter assembly that is closest to a subject during catheter insertion. Conversely, the term "proximal", as used herein, refers the direction lying along the axis parallel to the needle that is farther away from the subject when the catheter is inserted into the vein of the subject—that is, opposite to the distal direction.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future-filed applications claiming priority to this application may claim the disclosed subject matter in a different manner and generally may include any set of one or more features as variously disclosed or otherwise demonstrated herein.

EXAMPLES

The following examples describe details of some of the embodiments disclosed herein. The first example is an intravenous catheter assembly that includes a catheter tube having a proximal end and a distal end. A catheter hub is in fluid communication with the catheter tube and has proximal end, a distal end connected to the proximal end of the catheter tube, and a side port that provides fluid communication to an integrated extension tube. An elastomeric septum is positioned at least partially inside of the catheter hub. An introducer is movable between a ready for use position and a safe position and includes a needle hub, an introducer needle and a safety feature. The introducer needle has a proximal portion connected to the needle hub and distal end having a sharp distal tip. The introducer needle is disposed, at least in part, within the catheter tube when the introducer needle is in a ready for use position and defines a flash indication space between the catheter tube and the introducer needle. The introducer needle further includes a lateral surface that defines a relief that is positioned under the distal end of the catheter tube when the introducer is in the ready for use position to provide a flow path into the flash indication space. The safety feature is positioned to prevent access to the sharp distal tip of the introducer needle when the introducer is in the safe position.

Example 2 is the intravenous catheter assembly of example 1, wherein a septum length is defined by a length from a proximal end to a distal end of the septum taken h in a direction parallel to the introducer needle and a relief distance is defined from the sharp distal tip of the introducer needle to a proximal end of the relief, the relief distance being greater than the septum length.

Example 3 is the intravenous catheter assembly of any of examples 1-2, wherein the relied includes a flat, machined surface.

Example 4 is the intravenous catheter assembly of any of examples 1-3, wherein the relief is positioned on a chord that extends across a cross section of the introducer needle.

Example 5 is the intravenous catheter assembly of any of examples 1-4, wherein the relief lies at an angle to the introducer needle.

Example 6 is the intravenous catheter assembly of any of examples 1-5, wherein the relief includes a plurality of reliefs.

Example 7 is the intravenous catheter assembly of example 6, wherein the plurality of reliefs are positioned on different lateral sides of the introducer needle.

Example 8 is the intravenous catheter assembly of any of examples 1-7, wherein the relief extends in a spiral about the introducer needle.

Example 9 is the intravenous catheter assembly of any of examples 1-8, wherein the needle defines an internal lumen that extends from the proximal portion to the distal end of the introducer needle.

Example 10 is the intravenous catheter assembly of example 9, wherein the relief includes a slot that extends to the interior of the internal lumen from the flash space.

Example 11 is the intravenous catheter assembly of any of examples 1-10, wherein the relief has a depth of between 0.001 inches and 0.004 inches.

What is claimed is:

1. An intravenous catheter assembly comprising:
    a catheter tube having a proximal end and a distal end;
    a catheter hub in fluid communication with the catheter tube and having a proximal end, a distal end connected to the proximal end of the catheter tube, and a side port that provides fluid communication to an integrated extension tube;
    an elastomeric septum positioned at least partially inside of the catheter hub;
    an introducer that is movable between a ready for use position and a safe position, the introducer including a needle hub, an introducer needle and a safety feature;
    wherein the introducer needle has a proximal portion connected to the needle hub and a distal end having a bevel extending distally in a sharp distal tip, the introducer needle being disposed, at least in part, within the catheter tube when the introducer needle is in the ready for use position and defining a flash indication space between the catheter tube and the introducer needle, the introducer needle further including a lateral surface that defines a flat relief that is positioned under the distal end of the catheter tube when the introducer is in the ready for use position to provide a flow path into the flash indication space, and a bump on a lateral side of the introducer needle, the bump being disposed proximally to a proximal end of the flat relief;
    wherein the flat relief has a distal end proximal to the bevel;
    wherein the safety feature is positioned to prevent access to the sharp distal tip of the introducer needle when the introducer is in the safe position; and
    wherein a septum length is defined by a length from a proximal end to a distal end of the septum taken in a direction parallel to the introducer needle and a relief distance is defined from the distal end of the relief to the proximal end of the relief, the relief distance being greater than the septum length.

2. The intravenous catheter of claim 1, wherein the relief is positioned on a chord that extends across a cross section of the introducer needle.

3. The intravenous catheter of claim 1, wherein the relief lies at an angle to the introducer needle.

4. The intravenous catheter of claim 1, wherein the relief includes a plurality of reliefs.

5. The intravenous catheter of claim 4, wherein the plurality of reliefs are positioned on different lateral sides of the introducer needle.

6. The intravenous catheter of claim 1, wherein the relief extends in a spiral about the introducer needle.

7. The intravenous catheter of claim 1, wherein the introducer needle defines an internal lumen that extends from the proximal portion to the distal end of the introducer needle.

8. The intravenous catheter of claim 1, wherein the relief has a depth of between 0.001 inches and 0.004 inches.

* * * * *